(12) United States Patent
Cheong

(10) Patent No.: US 6,326,410 B1
(45) Date of Patent: Dec. 4, 2001

(54) WOUND DRESSING COMPRISING POLYURETHANE FOAM

(75) Inventor: Catherine Louise Cheong, Burnley (GB)

(73) Assignee: Johnson & Johnson Medical, Inc., Somerville, NJ (US)

( * ) Notice: Subject to any disclaimer, the term of this patent is extended or adjusted under 35 U.S.C. 154(b) by 0 days.

(21) Appl. No.: 08/436,688

(22) Filed: May 8, 1995

Related U.S. Application Data

(62) Division of application No. 07/971,488, filed on Nov. 4, 1992, now abandoned.

(51) Int. Cl.$^7$ .................................. C08J 9/08; C08L 75/04
(52) U.S. Cl. ........................... 521/67; 521/117; 521/137; 521/159; 521/174; 521/914
(58) Field of Search .................... 521/67, 117, 137, 521/159, 174, 914

(56) References Cited

U.S. PATENT DOCUMENTS

| | | | |
|---|---|---|---|
| 2,993,013 | * 7/1961 | Wolfe, Jr. ............................... | 521/67 |
| 3,178,300 | * 4/1965 | Gemeinhardt et al. .............. | 521/117 |
| 4,158,087 | * 6/1979 | Wood .................................. | 521/137 |
| 4,339,550 | 7/1982 | Palinczar et al. ...................... | 521/99 |
| 4,454,251 | * 6/1984 | Frisch et al. .......................... | 521/117 |
| 4,715,746 | * 12/1987 | Mann et al. .......................... | 521/117 |
| 4,725,627 | * 2/1988 | Arnason et al. ...................... | 521/67 |
| 4,920,172 | 4/1990 | Daoud ................................. | 524/502 |
| 5,064,653 | 11/1991 | Sessions et al. ...................... | 424/445 |

FOREIGN PATENT DOCUMENTS

| | | |
|---|---|---|
| 0 171 268 | 2/1986 | (EP) . |
| 0 189 178 | 7/1986 | (EP) . |
| WO 88/01878 | 3/1988 | (EP) . |
| 0 335 669 | 10/1989 | (EP) . |
| 57155224 | * 9/1982 | (JP) ....................................... 521/67 |

OTHER PUBLICATIONS

Hawley's Condensed Chemical Dictionary, 111th ed., (1987), P1018.

* cited by examiner

*Primary Examiner*—Rabon Sergent

(57) ABSTRACT

A wound dressing has a wound-contact layer formed from a polyurethane foam. The foam comprises one part by weight of the reaction product of an isocyanate-capped prepolymer with water (and optionally other hydroxy-functional compounds), and from 0.03 to 0.3 parts by weight of a natural or synthetic rubber. The isocyanate-capped prepolymer is preferably an isocyanate-capped ethyleneoxy/propyleneoxy copolymer, and the rubber is preferably an acrylic rubber.

9 Claims, 1 Drawing Sheet

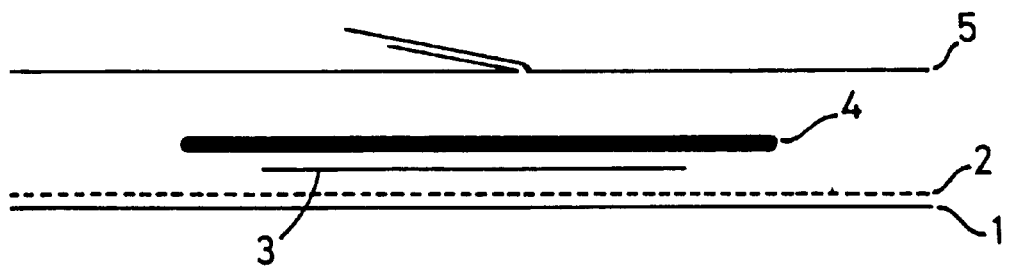

WOUND DRESSING COMPRISING POLYURETHANE FOAM

This is a division, of application Ser. No. 07/971,488, filed Nov. 4, 1992 now abandoned, which is hereby incorporated by reference.

This invention relates to a wound dressing having a wound contact layer formed from a polyurethane foam, and more particularly a conformable, high-density polyurethane foam. The invention also relates to a method for forming such a foam.

Polyurethane foams have been proposed for a number of uses in the prior art, and a wide variety of additives have been included in such foams, depending on the particular end use which is contemplated. For example, U.S. Pat. No. 3,961,629 discloses a hydrophilic polyurethane foam for use as an absorbent pad for body fluids. The cells of the foam have a coating of surfactant, and this is said to accelerate absorption of body fluids into the foam at medically acceptable rates. It is proposed that hygroscopic agents such as glycerol may also be incorporated into the foam, as may germicidal and therapeutic agents.

EP-A-0171268 discloses a dressing for use in deep wounds, which dressing comprises individual pieces of an absorbent hydrophilic foam contained within a porous bag formed from an apertured polymeric film. The absorbent foam is preferably a hydrophilic polyurethane foam which can be made from HYPOL isocyanate-capped polyether prepolymer marketed by W. R. Grace & Co., and non-ionic surfactants. Physiologically active components such as local anaesthetics, antibacterial agents and antifungal agents are proposed as additives which may be included in the foam.

According to EP-A-0171268, the fact that the foam is present in the form of individual pieces confers on the dressing the property of being able to conform to the contours of a wound cavity both on initial application of the dressing and subsequently following absorption of body fluids. It is said that existing commercially available foams, if used as a single piece, have too high a density to possess the required degree of conformability.

U.S. Pat. No. 4,339,550 discloses a hydrophilic foam composition which is prepared by the "in situ" reaction of an isocyanate-capped polyether prepolymer having a functionality of from about 2 to about 8, water, and a chemically compatible, essentially non-polar, volatile organic compound. The foam is stated to be capable of achieving a sustained, controlled release of the volatile materials from the foamed structure. Suitable "control release" ingredients include polyols, such as propylene glycol and glycerine.

EP-A-0335669 discloses a hydrophilic foam composition comprising the "in situ" reaction product of an isocyanate-capped polyether prepolymer, a hydrophilic agent capable of absorbing water, an adjuvant comprising an alcohol, a wetting agent and water. One application which is proposed for the foam composition is in the manufacture of wound dressings. The composition is said to carry the adjuvant releasably, so that at least a portion of the adjuvant is released into an external liquid (e.g. wound exudate) with which the foam composition comes into contact.

A wide range of prepolymers, hydrophilic agents, adjuvants and wetting agents are proposed in EP-0335669. Water soluble monohydric, dihydric and polyhydric alcohols are all said to be suitable adjuvants, but glycerol is preferred.

The present invention is based on the unexpected finding that polyurethane foams having properties which render them particularly suitable for use as wound contact layers may be obtained by including a natural or synthetic rubber in the foam composition. Indeed, the foams of the invention display the very combination of high density and high conformability which EP-A-0171268 indicates to be unattainable in prior art foams.

Accordingly, the present invention provides a wound dressing having a wound-contact layer formed from a polyurethane foam, said foam comprising a) one part by weight of the reaction product of an isocyanate-capped prepolymer with water and optionally other hydroxy-functional compounds, and b) from 0.03 to 0.3 parts by weight of a natural or synthetic rubber.

Preferably, the composition comprises one part by weight of the polyurethane reaction product and from 0.05 to 0.2 parts (e.g. from 0.05 to 0.15 parts) by weight of the rubber.

The addition of a natural or synthetic rubber has the effect of increasing the cure time for the polyurethane, and increases extensibility, strength and tack. Most importantly, it substantially reduces shrinkage of the gel on drying, and it also improves bubble formation, producing more regular, smaller bubbles.

If the rubber content is less than 0.03 parts per part of polyurethane reaction product, the effect on shrinkage of the gel may be too small to be of significant benefit. On the other hand, if the rubber content is too high, then the absorbency of the foam may be unacceptably low.

Preferably, the isocyanate-capped prepolymer has an NCO content of from 0.5 to 1.2 meq/g. Isocyanate-capped prepolymers having an isocyanate content within this range have been used in the prior art to produce so-called hydrogels. For this purpose, the prepolymers are mixed with relatively large quantities (eg. a ten-fold excess by weight) of water. The reaction mixture is initially of low viscosity, such that carbon dioxide which is evolved by reaction of the water with isocyanate end groups escapes. In this way, substantially no carbon dioxide is trapped within the hydrogel end product.

In contrast, the use of a relatively small amount of water produces an initial reaction mixture of much higher initial viscosity. Carbon dioxide formed by hydrolysis of isocyanate end groups is therefore trapped, producing a foamed hydrogel.

The prepolymer which is used in the method of the invention is preferably an isocyanate-capped polyether, such as an ethyleneoxy/propyleneoxy copolymer. A particularly suitable prepolymer is that available under Trade Mark HYPOL Hydrogel.

The foams of the invention generally have a density of at least 0.28 g/cm$^3$, and preferably at least 0.30 g/cm$^3$. Particularly preferred foams have a density in the range 0.32 to 0.48 g/cm$^3$, e.g. about 0.35 g/cm$^3$.

The foams of the invention generally also have an elongation at break of at least 150%, and more preferably at least 300%. Particularly preferred foams according to the invention have an elongation at break in the range from 500 to 2000%.

Depending principally on the amounts of rubber and other additives which are included, the foams of the invention typically have an absorbency of at least 3 g saline/g, preferably at least 5 g/g, and more preferably from 8 to 20 g/g. The foams are thus highly absorbent, yet conformable.

The preferred foams of the present invention also have the property of swelling and expanding when water is absorbed. This is particularly advantageous in a wound contact layer, because the swelling of the foam causes it to move inwards towards the wound bed, thus filling the wound cavity. This encourages the wound to heal from the base upwards and outwards, and it discourages epithelialization over the wound surface before the bed has been filled with granulation tissue.

The degree of swelling of the foams of the present invention on complete saturation with an aqueous medium is typically at least 100% (expressed in terms of the increase in volume), and preferably at least 200%. Preferred foams swell by 400 to 800%. Despite this high degree of swelling, however, the foams of the invention retain their integrity even after absorption of large quantities of water.

Moreover, the preferred foams according to the invention are found to have a morphology which is particularly appropriate for low adherence wound dressings. The foams are open-celled, the cells being very regular in size and shape, with very smooth edges to the pores in the walls of the cells. Typically, the cells of the foams of the invention have an average diameter in the range 0.1 to 0.6 mm.

In order to increase the softness and conformability of the foam and to facilitate processing, it is preferred to include a minor amount of a hydroxy functional compound in the foaming mixture. Suitable hydroxy functional compounds include lower monohydric alcohols such as methanol, ethanol and propanol, as well as dihydric and polyhydric alcohols such as ethylene glycol and glycerol. A particularly suitable polyol is sold by Bayer AG under the Trade Mark Levagel.

If an alcohol is included in the foaming mixture, traces of the alcohol are likely to remain in the free form after the foaming reaction. In the case of dihydric and polyhydric alcohols, these traces may be difficult to remove from the foam merely by heating. The use of higher boiling alcohols is therefore preferably avoided if the foam is to be used as a wound contact layer, because of the likelihood that such alcohols will be leached from the foam during use of the dressing.

The foams of the invention preferably contain less than 1% by weight of water soluble alcohols, and more preferably less than 0.1% by weight. It is particularly preferred that the foams of the invention are essentially free of water soluble alcohols (eg. less than 0.01% by weight).

Of the monohydric alcohols, methanol is particularly preferred because it is most effective in reducing the rate of reaction between the isocyanate-capped prepolymer and water. A reduction of the reaction rate is desirable in order to facilitate mixing of the various components and spreading of the reaction mixture into a layer of suitable thickness for curing.

The natural or synthetic rubber is preferably included in the foaming composition in the form of a latex, ie. a suspension or emulsion of the rubber in an aqueous medium. The latex will generally comprise 40 to 70% solids by weight, e.g. 50 to 60% by weight.

The rubber must of course be pharmaceutically acceptable. Acrylic-based rubbers are particularly preferred. These are commercially available in the form of latexes, such as PRIMAL N-582 and RHOPLEX N-560, manufactured by the Rohm & Haas company.

Alternative rubber compositions which can be used include COPYDEX adhesive (manufactured by Henkel), which is a latex of natural rubber containing about 56.2% solids by weight. Also suitable is COW GUM (manufactured by Cow Proofings Limited), which is a natural rubber in a hydrocarbon solvent containing about 28% solids by weight.

For use as a wound-contact layer, the foams of the invention may also include topical medicaments and antiseptics, such as silver sulphadiazine, povidone iodine, chlorhexidine acetate and chlorhexidine gluconate, as well as other therapeutically useful additives such as polypeptide growth factors and enzymes.

The present invention also provides a wound dressing comprising a wound contact layer formed from a polyurethane foam as described above, in conjunction with a water-repellant or water-impermeable backing layer. It is greatly preferred that the backing layer also be moisture vapour permeable, as well as being extensible and conformable. A particularly suitable material is a high density polyurethane foam, such as MEDIFIX 4003 or 4005. These are polyurethane foams of a blocked toluene diisocyanate nature, and are predominantly closed cell.

A particularly advantageous presentation for the dressing of the invention is as an island of wound-contact material on a backing layer, wherein at least the marginal portions of the backing layer are coated with adhesive. Any medically acceptable, skin friendly adhesive is suitable, including acrylic, hydrocolloid, polyurethane and silicone based adhesives.

The adhesive may be applied either continuously or discontinuously over the marginal portions of the backing layer. Preferably, however, the adhesive is applied continuously over the whole of the backing layer if the backing layer is not itself impermeable to bacteria, so as to ensure that the backing layer/adhesive combination is impermeable to bacteria.

It is also preferred that the combination of adhesive and backing layer have a minimum moisture vapour permeability of 400 $g/m^2/24$ hrs, and preferably at least 700 $g/m^2/24$ hrs.

The preferred adhesive is a polyurethane gel material known as LEVAGEL and marketed by Bayer AG. This adhesive is made up of three components, namely a modified diphenylmethane diisocyanate, high molecular weight polyhydroxy polyether and a catalyst (dibutyltindilaurate). These three components may be mixed such that the gel contains 4–10 parts (preferably 4.6–6.4 parts) of the modified diphenylmethane diisocyanate, 99.9–99.9975 parts, (preferably 99.94–99.995 parts) of the polyhydroxy polyether and 0.0025–0.1 parts (preferably 0.005–0.06 parts) of the catalyst.

The gel may be mixed by the methods given in U.S. Pat. No. 4,661,099 and applied by conventional coating methods to the backing. The thickness of the gel layer may be between 0.001 mm and 1.0 mm, and preferably between 0.05 mm and 0.5 mm, giving a coating weight of between 25 $g/m^2$ and 250 $g/m^2$.

The dressing may also contain a wicking layer between the wound contact layer and the backing layer. Such a wicking layer provides absorbency, but more importantly it encourages moisture to move from the wound facing side of the dressing to the back of the dressing where it escapes out of the dressing through the breathable backing. It should have good wicking properties so that moisture can be spread over as large a surface area as possible, thus increasing evaporation. The overall effect of this layer is to draw moisture from the wound facing layer, thus decreasing the chances of wound maceration, and to increase evaporation through the backing of the dressing.

The wicking layer may be formed of several plies (which may or may not be the same) if desired, but it is preferred that the total thickness of the wicking layer does not exceed 1 mm. It is also preferred that the wicking layer be substantially the same size and shape as the wound-facing layer, or slightly smaller than the wound-facing layer.

Suitable materials for the wicking layer include nonwoven, woven and knitted fabrics. Nonwoven viscose fabrics such as those conventionally used for making non-woven surgical swabs are preferred, but it will be understood that many alternative fabrics (particularly other cellulosic fabrics) could be used in their place.

The dressings of the invention will generally be sterile and enclosed in a conventional bacteria-proof envelope. Sterilization may conveniently be carried out using γ-irradiation, but other sterilization methods such as electron beam sterilization may also be used.

The present invention is further illustrated by the following examples and with reference to the accompanying drawing, which is a schematic section through a dressing according to the invention.

EXAMPLE 1

PREPARATION OF POLYURETHANE FOAM

Acrylic emulsion (PRIMAL N-582; 10 g) was mixed with deionised water (34 g) with a spatula in a disposable cup. Methanol (6 g) was added to HYPOL FHP 2002 prepolymer (50 g) in a disposable cup and mixed thoroughly for a few seconds. The acrylic/water mixture was then added to the HYPOL mixture and stirred. The foaming mixture was then poured onto release paper and spread using a stainless steel hand spreader set at a gap of 2.2 mm. The foam was left to cure and the foam sheet and release paper were placed in an oven (80° C.–100° C.) (30 min) to drive off the water. After cooling, the foam was lifted from the release paper, allowed to shrink, and replaced on the same paper. The foam was then kiss-cut to size and shape.

In an alternative procedure, the components were mechanically mixed using a commercially available two component polyurethane meter/mix dispense machine. The HYPOL prepolymer was placed in one pot and the acrylic latex, water and methanol were pre-mixed and placed in the second pot.

The foam had a density of 0.42 g/cm$^3$, and was highly conformable and elastic.

EXAMPLE 2

The procedure of Example 1 was followed, except that HYPOL Hydrogel (NCO content 0.5–1.2 meq/g) was used instead of HYPOL FHP 2002. The resulting foam had a density of 0.35 g/cm$^3$, an elongation at break of 1000%, and was capable of absorbing 8.5 g saline/g.

The foam produced in this example was formed into a wound dressing as shown schematically in FIG. 1. The dressing comprises a backing layer 1, in the form of a conformable, waterproof, extensible breathable film or foam, which is coated with a continuous or discontinuous layer of skin friendly adhesive 2. Centrally located on the backing layer 1 is a wicking layer 3 of absorbent material, and this in turn is covered by a wound contacting layer 4 of the polyurethane foam. Prior to use, the adhesive layer 2 and the wound contacting layer 4 are covered by a protective release paper 5 of conventional form. This is removed when the dressing is required, to expose the adhesive-coated margins of the backing layer 1 around the wound contacting layer.

EXAMPLE 3

EFFECT OF DIFFERENT PREPOLYMER CONCENTRATIONS

Five different formulations of wound-contacting layer were prepared by the method of Example 1. Each used water and HYPOL Hydrogel prepolymer in differing proportions, together with 10% w/w of acrylic emulsion (PRIMAL N-582) and 6% w/w methanol. The wound-contacting layers so prepared were then tested for absorbency. The results were as follows:

| HYPOL hydrogel | 70% | 65% | 50% | 40% | 35% |
|---|---|---|---|---|---|
| Absorbency Saline g/g | 3.2 | 5.6 | 8.5 | 7.8 | 3.7 |

EXAMPLE 5

EFFECT OF LATEX CONCENTRATION ON CURE RATE

Formulations were prepared as described in Example 1, except that the amount of PRIMAL N-582 was increased to 20% or 30%, with a corresponding reduction in the amount of water. The time taken for curing of the mixture at ambient temperature was increased from 2 mins (for 10% PRIMAL) to 2 min 10 sec (for 20% PRIMAL) and 2 min 40 sec (for 30% PRIMAL).

EXAMPLES 6–11

Further formulations based on Hypol Hydrogel prepolymer, methanol, PRIMAL N-582 and Levagel polyol were prepared in accordance with Example 1 as follows:

| Ex. No | Hypol (g) | Water (g) | PRIMAL (g) | MeOH (g) | Levagel (g) |
|---|---|---|---|---|---|
| 6 | 25 | 18.5 | 4 | — | 2.5 |
| 7 | 25 | 14.5 | 4 | 4 | 2.5 |
| 8 | 25 | 16.5 | 4 | 2 | 2.5 |
| 9 | 25 | 15.5 | 4 | 3 | 2.5 |
| 10 | 25 | 14.5 | 5 | 3 | 2.5 |
| 11 | 25 | 13.5 | 6 | 3 | 2.5 |

In each case, the resulting foam was highly absorbent, highly conformable, and had a density of at least 0.28 g/cm$^3$.

EXAMPLE 12

Example 1 was repeated, except that COPYDEX adhesive (Henkel; 56.2% solids) was used in place of PRIMAL N-582. The resulting foam cured in 2 minutes, had a density of 0.36 g/cm$^3$ and an elongation at break of 1500%, and was capable of absorbing 7.6 g of saline per g.

EXAMPLE 13

Example 1 was repeated, except that COW GUM adhesive (Cow Proofings Limited; 28% solids) was used in place of PRIMAL N-582. The resulting foam cured in 1.5 minutes, had a density of 0.37 g/cm$^3$ and an elongation at break of 1100%, and was capable of absorbing 7.1 g of saline per g.

What is claimed is:

1. A method of forming a polyurethane foam suitable for use as a wound-contacting layer, said method comprising the steps of:

mixing 1 part by weight of an isocyanate-capped prepolymer having from 0.5 to 1.2 meq NCO groups/gm with from 0.012 to 0.21 parts by weight of rubber solids in the form of a rubber latex and from 0.509 to 1.18 parts by weight of water, wherein the weight portion of water includes any water contained within the rubber latex;

then driving water from the product thereby produced.

2. A method according to claim 1 wherein the reaction mixture also contains from 0.05 to 0.4 parts by weight of a $C_1$ to $C_3$ monohydric alcohol.

3. A method according to claim 1 wherein the isocyanate-capped prepolymer is an isocyanate-capped polyether prepolymer.

4. A method according to claim 2 wherein the isocyanate-capped prepolymer is an isocyanate-capped polyether prepolymer.

5. A method according to claim 3 wherein the isocyanate-capped polyether prepolymer is an isocyanate-capped ethyleneoxy/propyleneoxy copolymer.

6. A method according to claim 4 wherein the isocyanate-capped polyether prepolymer is an isocyanate-capped ethyleneoxy/propyleneoxy copolymer.

7. A method according to claim 3 wherein one part by weight of the isocyanate-capped prepolymer is mixed with from 0.6 to 0.9 parts by weight of water.

8. A method according to claim 1 wherein one part by weight of the isocyanate-capped prepolymer is mixed with water in the presence of from 0.1 to 0.25 parts by weight of methanol or from 0.1 to 0.3 parts by weight of ethanol.

9. A method according to claim 5 wherein one part by weight of the isocyanate-capped prepolymer is mixed with water in the presence of from 0.1 to 0.25 parts by weight of methanol or from 0.1 to 0.3 parts by weight of ethanol.

* * * * *